United States Patent [19]

Yates

[11] 3,979,466

[45] Sept. 7, 1976

[54] PROCESS FOR CONDENSATION OF ALCOHOLS

[75] Inventor: James E. Yates, Ponca City, Okla.

[73] Assignee: Continental Oil Company, Ponca City, Okla.

[22] Filed: Sept. 19, 1974

[21] Appl. No.: 507,304

Related U.S. Application Data

[62] Division of Ser. No. 367,689, June 6, 1973, Pat. No. 3,860,664.

[52] U.S. Cl. ............................................. 260/642 C
[51] Int. Cl.² ......................................... C07C 29/00
[58] Field of Search ............. 260/642 C; 252/431 C

[56] References Cited
UNITED STATES PATENTS

| | | | |
|---|---|---|---|
| 1,984,884 | 12/1934 | Zazier | 260/156 |
| 2,064,254 | 12/1936 | Fuchs et al. | 260/642 C |
| 2,116,552 | 5/1938 | Arnold et al. | 260/156 |
| 2,457,866 | 1/1949 | Carter | 260/642 C |
| 2,836,628 | 5/1958 | Miller | 260/642 C |
| 2,848,495 | 8/1958 | Villemy | 260/638 B |
| 3,119,880 | 1/1964 | Kollar et al. | 260/642 C |
| 3,318,891 | 5/1967 | Hausman et al. | 252/431 C |

Primary Examiner—Joseph E. Evans
Attorney, Agent, or Firm—Cortlan R. Schupbach, Jr.

[57] ABSTRACT

A process for producing higher molecular weight alcohols by forming a reaction mixture of at least one lower molecular weight primary or secondary alkanol having a methylene group adjacent the hydroxylated carbon atom, an alkali catalyst and a palladium (II) compound, said palladium compound being mixed with the alkanol prior to dissolution of the alkali catalyst therein, and heating the reaction mixture to effect condensation of the alkanol while simultaneously removing water as it forms.

5 Claims, No Drawings

PROCESS FOR CONDENSATION OF ALCOHOLS

This is a division, of application Ser. No. 367,689 filed June 6, 1973 now U.S. Pat. No. 3,860,664.

This invention relates to the condensation of alcohols to form alcohol products of higher molecular weight. More particularly, the invention relates to an improvement in the condensation of primary and/or secondary alcohols having a methylene group adjacent to the hydroxylated carbon atom to produce alcohols having a carbon content equal to the sum of the carbon atoms of the two reactant alcohols and which are branched at the beta carbon atom.

According to the well-known Guerbet reaction, a primary or secondary alcohol which contains a methylene group adjacent to the hydroxylated carbon atom may be condensed with itself or with another alcohol of the same class to form a higher alcohol containing the sum of the carbon atoms of the reactant alcohols as the principal product. The classic catalyst for the Guerbet reaction is a strong alkali such as sodium metal, which is generally in the form of its alcoholate during reaction, sodium and potassium hydroxides and the like. Many theories have been advanced as to the particular mechanism of the reaction (for example, see U.S. Pat. No. 2,004,350; U.S. Pat. No. 2,971,033; U.S. Pat. No. 2,829,177 and U.S. Pat. No. 3,558,716) and, as indicated in U.S. Pat. No. 2,762,847, there is little general agreement as to what reaction or reactions actually occur during transformation of the lower alcohols to the higher alcohols. It is further indicated that a plurality of different reactions are likely involved so that the process is highly sensitive and unpredictable as to the effect of particular catalysts.

The overall reaction, of course, produces a reaction product mixture which not only contains the higher alcohols but also corresponding higher aldehydes and higher unsaturated alcohols and aldehydes as well as various other by-products due to side reactions. The higher aldehydes and higher unsaturated alcohols and aldehydes present little difficulty since upon hydrogenation of the reaction product they are converted to the desired higher alcohols. The other by-products which have been mentioned in the art include carboxylic acids as well as salts and esters thereof, and ordinarily it is desirable to minimize their formation. One technique for reducing by-products, which is suggested in U.S. Pat. No. 3,328,470, involves the use of less than 3 mol percent alkali catalyst and temperatures in the range of 200°–300°C while continuously removing water formed by the reaction. On the other hand, it is known that in achieving acceptable reaction rates relatively high temperatures (e.g. 290°C) and relatively large quantities of alkali catalyst must be employed, but under these conditions considerable unwanted by-products are also obtained. Thus, it was necessary to balance the reaction rate against the tolerable by-products in the standard Guerbet reaction.

Considerable activity has been involved in developing various approaches to attempt to improve the reaction rate of this process and, at the same time, reduce or at least not increase the by-products. Among the various approaches attempted are the use of certain phosphates as cocatalysts (U.S. Pat. No. 2,762,847); the use of a particular combination catalyst mixture made up of potassium carbonate, magnesium oxide and copper chromite (U.S. Pat. No. 2,971,033); the use of various dehydrogenation catalysts (see French Pat. No. 784,656; German Pat. No. 734,468; U.S. Pat. No. 2,457,866; U.S. Pat. No. 2,757,139; U.S. Pat. No. 2,836,628; German Pat. No. 784,040; German Pat. No. 911,730; German Pat. No. 855,108; German Pat. No. 855,107; and U.S. Pat. No. 2,829,177); and the use of platinum series metals (U.S. Pat. No. 3,514,493).

In addition to the above, it is indicated in U.S. Pat. No. 3,479,412 that the condensation reaction can be carried out at a temperature of the order of 100°C in a homogeneous alkaline solution by using a co-catalyst system comprising certain compounds of metals of the platinum series, which compounds are soluble in the reaction medium, together with a ligand selected from organic compounds of arsenic, antimony and phosphorus.

In accordance with this invention, it has unexpectedly been found that a significantly improved reaction rate may be obtained or, alternatively, significantly milder reaction conditions may be employed in the condensation of primary or secondary alkanols having methylene groups adjacent to the hydroxylated carbon atoms by carrying out the reaction in the presence of an alkali metal catalyst and certain palladium compounds as the sole required co-catalyst, provided that the palladium compound co-catalyst is introduced to the alkanol reactant prior to dissolution of the alkali metal catalyst therein. It is emphasized that no third catalyst component, such as a ligand, is required in carrying out the process of the invention.

The selectivity of the overall process of the invention is also maintained, as indicated by the hydrogenated product, compared with the standard Guerbet reaction. By selectivity, it is meant selectivity to the desired higher alcohols and precursors therefor such as higher aldehydes and higher unsaturated alcohols convertible to the desired higher alcohols by hydrogenation. While the remaining by-products remain the same quantitatively, their distribution is altered somewhat, namely, there is a reduction in the amount of dienes produced and a corresponding increase in higher boiling compounds. This feature is particularly advantageous when condensing alcohols of mixed carbon content since any dienes produced result in corresponding paraffins upon hydrogenation, some of which are not readily separable by simple distillation due to similarity of boiling points with the product higher alcohols. Thus, with reduced diene content there is a reduction in the paraffins which are not readily separable in such a situation.

In describing the invention in detail, the alkanols which may be used are primary or secondary alkanols having methylene groups adjacent to the hydroxylated carbon atoms. These alkanols may best be illustrated by the formula

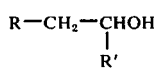

wherein each of "R" and "R'" can be hydrogen, an aryl group, or a straight or branch chain alkyl group. Preferably, R' is hydrogen and R is an alkyl group. While there is no limitation as to the number of carbon atoms the alkyl group may contain from a theoretical standpoint, more practical considerations indicate that such alkyl group most likely will contain about 1 to 28 carbon atoms. Thus, the most preferred alkanols are those which are branch or straight chain, have 2 to 30 carbon atoms and have a methylene group adjacent the hydroxylated carbon atom. Illustrative of these alkanols are 1-butanol; isopropyl alcohol; 1-octanol; 1-hexadecanol; 1-octadecanol; 1-eicosanol; 1-dodecanol; 1-hexacosanol; 4-methyl-pentanol-2; octanol-2; 1-tetracosanol; 1-pentanol; 1-tetradecanol; 3,3-dimethyl-1-butanol; 4-methyl-1-pentanol; 4-methyl-1-heptanol; 3-methyl-1-heptanol; 3,3-dimethyl-1-heptanol; 3,3-dimethyl-1-hexanol; 4,4-dimethyl-1-heptanol; 4,4-dimethyl-1-hexanol; 3,4-dimethyl-1-heptanol; 3,4-dimethyl-1-hexanol; phenylethanol; and the like. The alcohols may be reacted in their pure form or as mixtures. In particular, alcohol mixtures such as those generally referred to as "Oxo" alcohols having methylene groups adjacent to the hydroxylated carbon atoms are suitable as are mixtures of linear alkanols.

The above-described alkanols are generally condensed in the presence of an alkali catalyst and a specific palladium compound as co-catalyst by first introducing the palladium compound to the alkanol reactant, thereafter dissolving the alkali catalyst in the reaction medium before or during heating of the reaction mixture to the desired condensation temperature.

The alkali metal catalysts are well-known and fully described in the literature relative to Guerbet condensations of alcohols. These alkali catalysts include the alkali metals, alkali metal hydroxides, alkali metal oxides and alkali metal alcoholates. The metals, hydroxides and oxides will, of course, form the alcoholates in the reaction system wherein the hydrocarbon moieties of the alcoholate correspond to the hydrocarbon moieties of the alcohol reactants. When preformed alkali metal alcoholates are used it is not necessary that they correspond with the alcohol reactants. Illustrative of suitable catalysts are metallic sodium or potassium, lithium hydroxide, sodium hydroxide, potassium hydroxide, sodium oxide, potassium oxide, sodium alcoholates, potassium alcoholates, and the like. Obviously other alkali metal compounds may be used provided that they will form the corresponding alcoholates under reaction conditions. Such compounds include the alkali metal bisulfites.

The amount of alkali catalyst employed forms no part of this invention and the effects of various quantities of such catalyst are known in the art. Since large quantities of alkali catalyst lead to increased amounts of unwanted by-products and since good reaction rates are achieved by the improvement of this invention with low levels of alkali catalyst, it is normally not desirable nor is it necessary to exceed an amount of alkali catalyst equivalent to about 4 mols of the alkali metal per 100 mols of alcohol reactants. Generally, an amount of alkali catalyst equivalent to about 0.1 to 4 mols of the alkali metal per 100 mols of alcohol reactants may be employed with satisfactory results, with preferred amounts being equivalent to about 0.5 to 4 mols of the alkali metal on the same basis.

The palladium compounds useful in the process of this invention include palladium (II) halides such as the chloride, bromide and iodide; palladium (II) alkylcarboxylates wherein the alkyl group has 1 to 17 carbon atoms such as palladium acetate, palladium butyrate, palladium 2-ethylhexanoate, palladium stearate, palladium propionate; and palladium (II) compounds of the formula $(Y)_2Pd(X)_4$ wherein Y is ammonium or an alkali metal, such as sodium or potassium, and X is a halogen, such as chlorine, bromine or iodine. Illustrative of this latter group of compounds are included $(NH_4)_2Pd(Cl)_4$; $(NH_4)_2Pd(Br)_4$; $Na_2PdCl$; $K_2PdCl_4$ and $K_2PdBr_4$.

The above palladium (II) compounds which are water soluble salts may be introduced to the alkanol reactants in the form of an aqueous solution for ease of handling and dispersibility of the alkanol reactant. The amount of water employed for this purpose should be minimized since water must be subsequently removed from the reaction mixture to avoid producing unwanted by-products as described hereinafter. Since the palladium (II) compounds are effective co-catalysts in very low amounts the amount of water introduced in this way is not normally great and presents little difficulty in removing later on in the process. Those which are not water soluble may be introduced in solution with the alkanol reactant or with an inert solvent or as is.

In general, catalytic amounts of the palladium (II) compounds may be employed. Usually, this will be an amount sufficient to provide at least about 1 ppm palladium metal based on the alkanol reactants. On the upper side, the limiting considerations are economics and the fact that increased amounts of palladium generally result in increased high-boiling by-products. For these reasons one probably will not employ amounts in excess of that which will provide about 50 ppm palladium metal based on the alkanol reactants. However, it is also pointed out that increased amounts of palladium do reduce the amount of diene formed during reaction but are not to the extent that it offsets the high-boiling by-products produced. Preferred amounts are in the range of about 1 to 10 ppm with 1 to 5 ppm being most preferred.

As mentioned previously, the manner in which the reaction mixture is prepared is critical to operation of the process. The palladium compound must be introduced to the alkanol reactants prior to dissolution of the alkali catalyst therein. If the reverse sequence of addition of these materials is employed the condensation reaction is severely inhibited or does not occur. The reason for this is not understood but the results have been demonstrated by laboratory work as described hereinafter in the examples. The addition of both the palladium compound and the alkali catalyst to the alkanol reactants must also be at temperatures below the reaction temperature (reflux), otherwise the desired effects of the palladium will be severely inhibited.

The reaction can generally be carried out over a wide range of temperatures similarly as is known in connection with Guerbet reactions. These temperatures will usually range from about 80°C to about 300°C, preferably from about 200°C to about 300°C. The particular temperature employed will depend upon the particular alkanol reactants, the particular alkaline condensing agent employed and other operating considerations as understood in the art.

It is essential that water initially present and that produced from the condensation reaction be removed as the reaction progresses, otherwise, the oxidation of the alcohols to carboxylic acids will be increased with a corresponding loss in alkali catalyst through subsequent neutralization of the acids. As indicated in the prior art, water removal from the Guerbet reaction may be effected by employing a dehydrating agent such as calcium oxide or magnesium oxide. However, it is preferred to remove water by azeotropic distillation. The latter procedure is particularly advantageous in the condensation of low molecular weight alcohol while operating under atmospheric and superatmospheric pressure.

In the process of the invention, it is generally desirable to employ alkali catalysts which contain a minimum of water since any water introduced with the catalyst must be removed as pointed out above and large amounts may also tend to inhibit the reaction. This is not to say that no water can be so introduced and in some cases it may be very advantageous from a materials handling point of view to add the alkali catalyst in the form of a reasonably concentrated aqueous solution.

Except as the above considerations may influence the conduct of the reaction, pressure is not an essential aspect of the process. However, it is desirable to maintain the reactants in a liquid state and thus sufficient pressure will be employed where necessary to achieve this physical state.

Inert diluents may be employed in the reaction as desired. Such diluents include hydrocarbons such as paraffins, olefins, benzene, toluene, xylene, etc.

As previously indicated, the reaction product from the condensation reaction will generally contain, in addition to the higher molecular weight saturated alcohols, higher molecular weight aldehydes and higher molecular weight unsaturated alcohols and aldehydes as well as certain minor amounts of other by-products. Because of the presence of the aldehydes and unsaturated alcohols and aldehydes, it is generally desirable to hydrogenate the reaction product before recovering the product alcohols. Standard techniques may be employed. This has the effect of converting the higher molecular weight aldehydes and unsaturated alcohols and aldehydes to the product alcohols and thus increases the overall yield of the desired product.

In recovering the product alcohols from the hydrogenated reaction product, conventional distillation techniques may be employed whereby unreacted lower molecular weight alcohols will first be separated followed by the product alcohols with the higher boiling by-products remaining behind in the distillation bottoms. When employing a single alkanol reactant any dimeric diene present in the reaction product will be converted to the corresponding paraffin upon hydrogenation and may be separated from the product higher alcohols through distillation. However, when a mixture of alcohol reactants are employed some of the dimeric dienes converted to paraffins upon hydrogenation will not be readily separable from the product higher alcohols by simple distillation due to the similarity in boiling points. This emphasizes again one of the previously mentioned advantages of the process when using mixed alkanol reactants wherein the distribution of by-products in the reaction is shifted from the dimeric dienes to the higher boiling by-products. By reducing the amount of dimeric dienes in the reaction product there results a decreased content of the contaminating paraffins in the product mixed alcohols after hydrogenation and recovery by distillation.

The invention is further illustrated by the following examples:

EXAMPLE 1

Comparative experiments were conducted to demonstrate the effectiveness of the improvement of the invention in significantly reducing reaction time while retaining relatively mild reaction conditions for the Guerbet reaction and in altering the distribution of by-products while substantially maintaining the selectivity of the process in producing higher alcohols and the higher saturated aldehydes, unsaturated aldehydes and unsaturated alcohols convertible to the higher alcohols upon simple hydrogenation.

The control experiment was conducted by charging 250 g (1.58 mol) of 1-decanol and 2.1 g (0.0318 mol) KOH pellets (85% KOH, 15% water) to a 500 ml three-necked flask equipped with a Dean-Stark azeotrope trap and reflux condenser, thermometer and stirrer. The reaction mixture was heated to reflux temperatures and maintained at reflux until about 8 ml water was produced and collected. This represented about 50% conversion of the 1-decanol, 1 ml water derived from the KOH pellets and 7 ml water from the condensation reaction. The time required to produce the last 7 ml of water was about 7.25 hours. The crude reaction mixture was acid washed with 25% $H_2SO_4$ followed by water washing to remove the alkali catalyst. After removing the water the entire reaction mixture was analyzed by gas chromatography which indicated about 51% by weight conversion of the 1-decanol. The reaction product analyzed as about 93% by weight saturated alcohol having 20 carbon atoms and alcohol precursor having 20 carbon atoms (saturated aldehyde and unsaturated aldehyde and alcohol), about 5% by weight dimeric diene having 20 carbon atoms and about 2% by weight higher-boiling by-products.

The process of the invention was then carried out in the same manner as described above except that 1 ml of an aqueous solution of $PdCl_2$ (1.25 mg Pd/ml of solution), equivalent to 5 ppm Pd metal based on the 1-decanol reactant, was introduced to the 1-decanol with agitation prior to dissolution of the KOH pellets therein. Thereafter, the reaction mixture was heated to reflux and held there (212°–243°C) until 9 ml of water were collected (1 ml in the KOH, 1 ml in the $PdCl_2$ solution and 7 ml produced by the condensation reaction). The time required to produce the last 7 ml of water was about 30 minutes. Work up of the reaction mixture was the same as described above. Gas chromatography analysis indicated a 1-decanol conversion of about 55% with the reaction product containing about 93.4% by weight saturated alcohol having 20 carbon atoms and alcohol precursor having 20 carbon atoms, about 1.1% by weight dimeric diene having 20 carbon atoms and about 5.6% by weight of higher boiling by-products.

The results of these tests are shown in Table I.

TABLE I

| Pd (ppm) | Reaction Time | Conversion (wt %) | $C_{20}$ Alcohol & $C_{20}$ Alcohol Precursor[a] (wt %) | Diene (wt %) | HB[b] (wt %) |
|---|---|---|---|---|---|
| 0 | 7.25 hr | 51 | 93 | 5 | 2 |

TABLE I-continued

| Pd (ppm) | Reaction Time | Conversion (wt %) | C₂₀ Alcohol & C₂₀ Alcohol Precursor[a] (wt %) | Diene (wt %) | HB[b] (wt %) |
|---|---|---|---|---|---|
| 5 | 30 min | 55 | 93.4 | 1.1 | 5.6 |

[a] includes unsaturated and saturated alcohol and unsaturated and saturated aldehyde
[b] readily separable higher-boiling by-products

EXAMPLE 2

To demonstrate the criticality of introducing the palladium salt to the alkanol reactant prior to dissolving the alkali catalyst therein the following tests were conducted.

In a first experiment, the general procedure described in Example 1 was followed except that the 2.1 g of KOH pellets were dissolved in the alkanol reactant prior to introducing the 1 ml of $PdCl_2$ solution (5 ppm Pd based on alkanol reactant). After the water attributed to the KOH pellets was collected the reflux conditions were continued for another 30 minutes during which time no water was detected evidencing that no condensation reaction was apparently taking place.

In a second experiment, the general procedure described in Example 1 was followed except that the 2.1 g of KOH pellets were dropped into the alkanol reactant but not dissolved followed immediately by introduction of the 1 ml of aqueous $PdCl_2$ (5 ppm Pd based on the alkanol reactant) and thereafter the KOH pellets were dissolved. Reflux conditions were then imposed. After removal of 1 ml water attributed to the KOH the reflux conditions were continued until an additional 7 ml of water were produced and collected, a time of about 54 minutes.

EXAMPLE 3

Another example of the process of the invention was carried out following the procedure described in Example 1 except that only 0.2 ml of the aqueous $PdCl_2$ solution (equivalent to about 1 ppm Pd metal based on the 1-decanol reactant) was introduced to the 1-decanol prior to dissolution of the KOH pellets. The reaction mixture was heated to reflux and after about 1.1 ml of water attributed to the KOH pellets and aqueous $PdCl_2$ solution were removed the reaction was continued until 7 ml of water were produced and collected from the condensation reaction. The time required was noted to be about 6.8 hours. Thus, even at 1 ppm Pd metal there is likely some improvement in the reaction rate as compared with no co-catalyst (see Table I) even taking into consideration experimental discrepancy.

EXAMPLE 4

The procedure of Example 3 was carried out except that about 0.4 ml of the $PdCl_2$ solution (equivalent to 2 ppm Pd metal based on the 1-decanol reactant) was employed. After about 1.3 ml of water was removed (attributed to KOH pellets and $PdCl_2$ solution) it was noted that about 2.1 hours were required to produce and collect the next 7 ml of water from the condensation reaction. In this example the reaction mixture was analyzed by gas chromatography indicating the actual conversion of 1-decanol to about 52%. The reaction product analyzed about 94.7% by weight saturated alcohol having 20 carbon atoms and alcohol precursors having 20 carbon atoms, 2.5% by weight dimeric diene having 20 carbon atoms and about 2.8% higher-boiling by-products.

EXAMPLE 5

Another embodiment of the process of the invention was carried out in accordance with the procedure described in Example 1 except that 1 ml of a solution of $(NH_4)_2PdCl_4$ (1.25 mg Pd/ml) was employed in place of the $PdCl_2$ solution (equivalent to about 5 ppm Pd metal based on the 1-decanol reactant). The time required to produce and collect the 7 ml of water from the condensation reaction (after accounting for the water from the KOH pellets and Pd solution) was about 0.8 hour.

EXAMPLE 6

In another embodiment of the invention the procedure described in Example 1 was followed using 1 ml of an aqueous solution of palladium (II) acetate (1.25 mg Pd/ml) in place of the $PdCl_2$ solution (equivalent to about 5 ppm Pd metal based on the 1-decanol). After removal of the water attributed to the KOH pellets and palladium solution, another 7 ml of water were produced and collected over a period of about 2.5 hours.

EXAMPLE 7

The ineffectiveness of Pd (IV) salts was demonstrated by repeating the procedure described in Example 6 except for employing 1 ml of an aqueous solution of $K_2PdCl_6$ (1.25 mg Pd/ml) in place of the palladium (II) acetate (equivalent to about 5 ppm Pd metal based on the 1-decanol). After removing water attributed to the KOH and aqueous palladium solution the reaction was continued for about one hour during which time only about 0.4 ml of water from the condensation reaction was produced and collected indicating less than about 5% conversion.

EXAMPLE 8

The ineffectiveness of dissolving the KOH in the 1-decanol reactant prior to introducing the Pd (II) compounds was further demonstrated by two experiments wherein the general procedure described by the first experiment in Example 2 was generally followed except that in both the water introduced with the KOH pellets was removed prior to introducing the Pd (II) compounds. One experiment (A) involved the use of 2.1 mg of crystalline $PdCl_2$ and the other experiment (B) involved the use of 0.1 ml of aqueous $(NH_4)_2PdCl_4$ solution (12.5 mg Pd/ml), both being equivalent to about 5 ppm Pd metal based on the 1-decanol reactant. In experiment A, refluxing for about 1.2 hours produced only 0.5 ml water indicating less than 7% conversion. In experiment B, refluxing for about 0.9 hours after removal of the water due to the aqueous palladium solution produced only about 0.2 ml water indicating less than about 5% conversion.

EXAMPLE 9

Another experiment was carried out following the procedure described in Example 5 except that 1 ml of aqueous $PdCl_2$ (1.25 mg Pd/ml) was employed and 0.126 g of powdered charcoal was added and the reaction mixture was heated and stirred for about 5 minutes at reflux before adding the KOH pellets. Reflux was then continued and, after accounting for the water introduced by the KOH and the aqueous palladium solution, it was noted that only 0.8 ml of water was produced and collected from the condensation reaction after one hour indicating about 10% conversion.

EXAMPLE 10

In two experiments demonstrating temperature effects, the procedure described in Example 9 was followed except that in one experiment (A) 0.1 ml of an aqueous solution of $(NH_4)_2PdCl_4$ (12.5 mg Pd/ml) was employed and in the other experiment (B) 1 ml of an aqueous solution of $(NH_4)_2PdCl_4$ (1.25 mg Pd/ml) was employed and in both experiments the reaction mixture was heated and maintained at about 100°C for about 15 minutes before adding the KOH pellets. After accounting for the water introduced by the KOH and the aqueous palladium solutions, it was noted that in experiment A about 1.7 ml of water was produced and collected after 0.75 hour indicating about 24% conversion and in experiment B about 0.9 ml of water was produced and collected after about 0.7 hour indicating about 10% conversion.

EXAMPLE 11

Two experiments were carried out as described in Example 5 except that in one experiment (A) 4.6 g of 45% aqueous KOH (2.4 mol % based on the 1-decanol) and 0.1 ml of an aqueous solution of $(NH_4)PdCl_4$ (12.5 mg Pd/ml) were employed and in experiment B 3.9 g of 45% aqueous KOH (2 mol % based on the 1-decanol) and 1 ml of aqueous $PdCl_2$ (1.25 mg Pd/ml) were employed. After accounting for the water introduced by the KOH and the aqueous palladium solutions, it was noted that in experiment A about .2 ml of water was produced and collected from the condensation reaction after about 0.5 hour indicating less than about 5% conversion and in experiment B about 7 ml of water was produced and collected from the condensation reaction after about 1.4 hours indicating about 50% conversion. While it is not understood why the results of these two experiments are so different it is believed that the palladium (II) catalysts used in the invention may be somewhat sensitive to water in the amounts present in the experiments.

Thus having described the invention in detail, it will be understood by those skilled in the art that certain variations and modifications may be made without departing from the spirit and scope of the invention as described herein and defined in the appended claims.

I claim:

1. A process for producing higher molecular weight hydrocarbon alcohols by forming a reaction mixture comprised of at least one lower molecular weight alkanol having a methylene group adjacent the hydroxylated carbon atom, an alkali catalyst and a catalytic amount of a palladium (II) alkyl carboxylate wherein the alkyl group has 1 to 17 carbon atoms, said palladium compound being mixed with alkanol prior to dissolution of the alkali catalyst therein with the reaction mixture being formed at temperatures below that necessary to effect condensation of the alkanol, and heating the reaction mixture from about 80°C to about 300°C to effect condensation of the alkanol, while simultaneously removing water as it forms, wherein the alkali catalyst is at least one catalyst selected from the group consisting of alkali metal, alkali metal hydroxide, alkali metal oxide, alkali metal bisulfite or alkali metal alcoholate.

2. A process according to claim 1 wherein a mixture of lower molecular weight alkanols is employed.

3. A process according to claim 1 wherein the palladium (II) alkylcarboxylate is employed in an amount sufficient to provide at least about 1 ppm palladium metal based on the alkanol reactant.

4. A process according to claim 3 wherein the amount of palladium (II) carboxylate is sufficient to provide 1 to 10 ppm palladium metal based on the alkanol reactant.

5. A process according to claim 1 wherein the palladium (II) alkylcarboxylate is palladium acetate or palladium 2-ethylhexanoate.

* * * * *

UNITED STATES PATENT OFFICE
CERTIFICATE OF CORRECTION

PATENT NO. : 3,979,466
DATED : September 7, 1976
INVENTOR(S) : James E. Yates

It is certified that error appears in the above-identified patent and that said Letters Patent are hereby corrected as shown below:

Column 2, line 4, "784,040" should be --748,040--.

Column 3, line 36, the word "alkali" should follow the word suitable.

Signed and Sealed this

Twenty-first Day of December 1976

[SEAL]

Attest:

RUTH C. MASON
*Attesting Officer*

C. MARSHALL DANN
*Commissioner of Patents and Trademarks*